United States Patent [19]

Broadwin et al.

[11] Patent Number: 4,949,601
[45] Date of Patent: Aug. 21, 1990

[54] APPARATUS FOR ASSEMBLING THREADED MEMBERS

[75] Inventors: Alan Broadwin, Brooklyn, N.Y.; Joseph N. Logan, Trumbull, Conn.

[73] Assignee: Valleylab, Inc., Boulder, Colo.

[21] Appl. No.: 421,209

[22] Filed: Oct. 13, 1989

[51] Int. Cl.⁵ .............................................. B25B 9/02
[52] U.S. Cl. .......................................... 81/52; 81/488
[58] Field of Search ................... 81/52, 467; 269/239, 269/47, 52

[56] References Cited

U.S. PATENT DOCUMENTS 4,832,021  5/1989  Kuhl et al. ............................ 81/467

Primary Examiner—Frederick R. Schmidt
Assistant Examiner—Lawrence Cruz
Attorney, Agent, or Firm—Peter C. Richardson; Lawrence C. Akers; Mark Dryer

[57] ABSTRACT

An apparatus for assembling and disassembling threadably engageable members, which comprises: (a) wrenching means and (b) an integral securing means and torque limiter assembly; said assembly comprising, in combination, securing means operatively associated with a pinion block pivotally mounted on a solid base, said pinion block having a surface which bears against biasing means connected to force means, preferably a compression spring, which provides a predetermined amount of torquing when a first member is held in said securing means and a second member is turned relative thereto by said wrenching means, whereby the amount of torquing is limited by the pivotal movement of said pinion block.

11 Claims, 3 Drawing Sheets

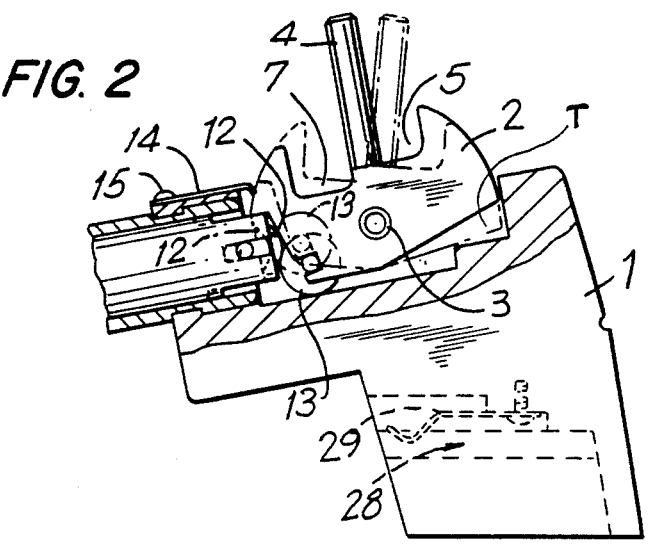
FIG. 2
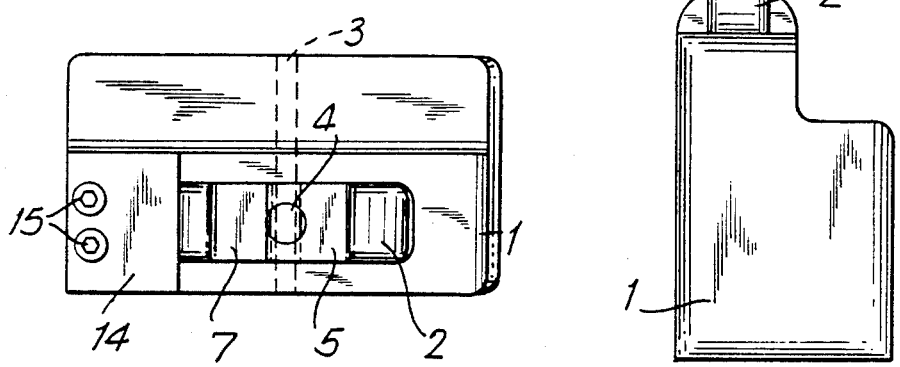
FIG. 3
FIG. 4
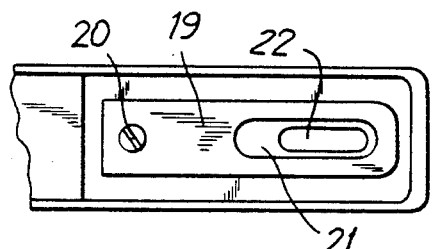
FIG. 5
FIG. 6

APPARATUS FOR ASSEMBLING THREADED MEMBERS

BACKGROUND OF THE INVENTION

This invention relates to an apparatus for assembling and disassembling the threadably engageable members of a device having two or more such members. In particular, the invention is concerned with an apparatus for the assembly and disassembly of interchangeable members of a surgical acoustic device.

Ultrasonic surgical devices for performing a number of surgical procedures are known in the art. A representative device is a hand-held instrument comprising a surgical handpiece incorporating a resonant vibrator having an electrically operated transducer which produces ultrasonic vibrations which are amplified and transmitted to a tool tip for the fragmentation of biological tissue. Typical examples of such a device are disclosed in U.S. Pat. Nos. 4,223,676 and 4,425,115.

The structure of an ultrasonic surgical device such as that disclosed in the aforementioned patents depends not only upon the technical and functional requirements of a resonant vibrator but also upon its surgical application. Thus, developments have been made over the years to determine the length and diameter of the tool required for a useful surgical device in various operative sites. Extensive experience has determined that an especially useful assembly can be made from a combination of members that are threaded together for easy interchange. The joint between the tool member and the adjacent member of the resonant vibrator is desirably made at a point which will provide maximum amplification at the tool tip. However, this is generally the point of greatest stress and requires a strong coupling to maintain the members in appropriate contact and avoid mechanical losses and damage during ultrasonic vibrations.

In practice, it is important that intimate contact be maintained between the threadably engaged members during operation of the device to maximize energy transfer, minimize mechanical losses and obtain consistent performance during surgical use. In particular, it is important to minimize parasitic vibrations during operation which may cause failure of either or both of the coupled acoustic members.

Experience with surgical devices also has determined an appropriate coupling force or torque for certain assemblies. The torque should be such that the acoustic members can not be adequately assembled with normal finger force; thus requiring a wrench with an appropriate mechanical advantage. Also, it necessarily follows that the members can not be disassembled without a wrench. Thus, an apparatus and method for assembling and disassembling the threadably engageable members of such devices has to be available in the art.

The technique of assembling and disassembling acoustic members of surgical devices is dependent upon a number of constraints. For example, the structure and size of the threaded joint between the members is desirably as small as possible to minimize the weight and to minimize visual interference with the surgical procedure. Because of such size constraint, overtightening of the threaded joint is undesirable since overtightening may overstress the joint, resulting in its fracture. In contrast, insufficient tightening can result in incomplete acoustic coupling, heating of the threaded joint, reduced surgical performance and a potential for failure of the acoustic parts.

U.S. Pat. No. 4,832,021 describes and claims an apparatus and method which satisfactorily deals with the above constraints and provides means whereby acoustic members may be properly assembled and disassembled. In particular, the apparatus of U.S. Pat. No. 4,832,021 comprises a surgical handpiece, a fixture comprising a body member, said body member including a defining means for defining a handpiece-receiving opening extending transversely therethrough for receiving said surgical handpiece therein, said body member including a securing means for securing said surgical handpiece in position in said handpiece-receiving opening, and a torquing wrench means, including a first socket having a first socket bore therethrough and which is open at both ends, which is retained in scissor-like cooperating relationship with said fixture for torquing an acoustic member to a predetermined torque value into place on said surgical handpiece, after passing an end of the acoustic member through said first socket bore, and while said securing means secures said surgical handpiece against rotation in and relative to said body member.

As stated above, the apparatus of U.S. Pat. No. 4,832,021 enables an operator to satisfactorily assemble acoustic members while applying the correct torque, but the apparatus itself comprises a number of distinct components which have to be assembled on and around the acoustic members to secure said members before the coupling torque is applied. Moreover, the torque limiting means is included in the wrench.

It has now been found that appropriate assembly and disassembly of threadably engageable members can be achieved by an apparatus which comprises only two operating components, wherein the component which holds and secures one of the members also includes the torque limiting means and the other component is the wrenching means, which accordingly may be simplified as hereinafter described.

SUMMARY OF THE INVENTION

In accordance with the present invention there is provided an apparatus for assembling and disassembling a device comprising at least a first and a second threadably engageable member, which apparatus comprises:
 (a) wrenching means and
 (b) an integral securing means and torque limiter assembly;
said assembly comprising, in combination, securing means operatively associated with a pinion block pivotally mounted on a solid base, said pinion block having a surface which bears against biasing means connected to force means which provides a predetermined amount of torquing when said first member is held in said securing means and said second member is turned relative thereto by said wrenching means, whereby the amount of torquing is limited by the pivotal movement of said pinion block.

Preferably the force means comprises a compression spring. Alternatively, the force means may be, for example, a torsion bar.

The invention also provides an apparatus as described above in which said compression spring has a proximal end and a distal end and is mounted in a hollow tubular member having a proximal end and a distal end, and said biasing means comprises a cylindrically shaped tappet having a distal end attached to the proximal end of said compression spring and a proximal end having a first roller attached thereto which first roller bears against a second roller attached to said surface of said pinion block.

In a preferred embodiment the securing means comprises, in combination, a handle having a proximal end and a distal end and being pivotally mounted at said distal end on an arm attached to the distal end of said hollow tubular member such that the pivotal movement of the handle defines an open position and a closed position, respectively, relative to the pinion block, a leaf spring having a central slot and being attached near the proximal end of the handle on the side facing the pinion block, and a post-shaped key integrally attached to the upper surface of the pinion block at a position such that said key passes through the slot in the leaf spring when the handle is in the closed position.

Preferably said handle has a spring clip which clips around said tubular member when the handle is in the closed position, thereby maintaining the assembly in the closed position until said spring clip is released.

Preferably the post-shaped key is so positioned on the upper surface of the pinion block that the profile of said upper surface defines grooves which, together with said key, are adapted to hold engageable members of different sizes.

Since the torque limiter of the invention is incorporated in the assembly which also includes the securing means, the wrenching means can be a simple flat wrench. A simple flat wrench, such as that illustrated in the drawings, is desirable because such a tool can be easily stored, when not in use, by a spring clip attached to the base of the torque limiter assembly or closely associated therewith.

Alternatively, the wrenching means may be a tubular socket wrench, an adjustable wrench, or a commercially available box wrench.

BRIEF DESCRIPTION OF THE DRAWINGS

The invention will be more particularly described with reference to a preferred embodiment as illustrated in the accompanying drawings, in which:

FIG. 2 is a side elevation of the solid base holding the pinion block of FIG. 1 showing the pinion block in both the rest position (as in FIG. 1) and the torqued position;

FIG. 3 is a top plan view of the base and pinion block of FIG. 2;

FIG. 4 is an end elevation of the base and pinion block of FIG. 2;

FIG. 5 is a bottom plan view of the proximal end of the handle of FIG. 1;

FIG. 6 is a cross-section through line 6—6 in FIG. 1;

DETAILED DESCRIPTION OF THE INVENTION

Figure 1:
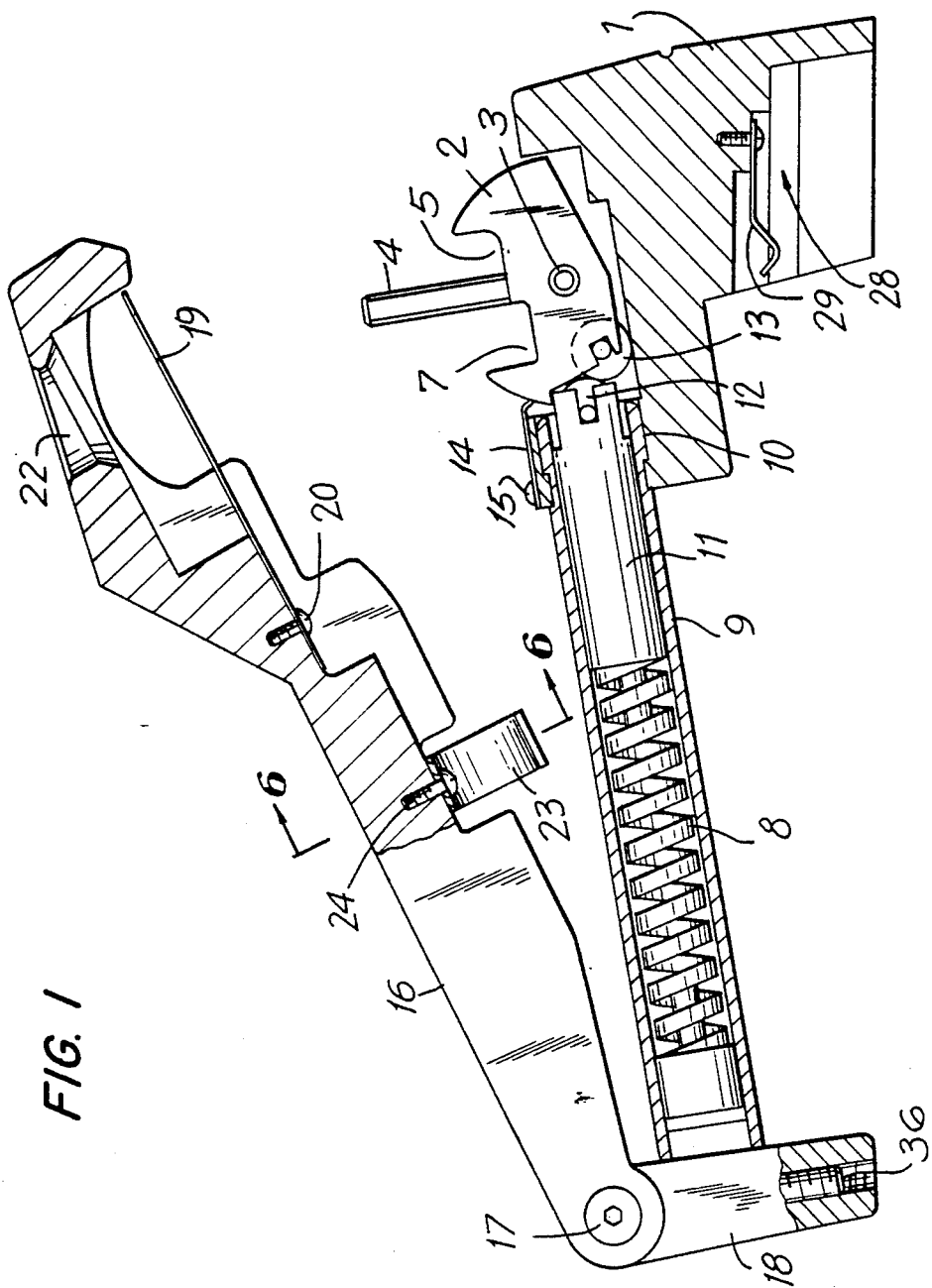
FIG. 1 is a side elevation, partly in section of a securing means and torque limiter assembly.

The preferred embodiment of the invention illustrated in FIG. 1 of the drawings comprises a solid base 1, shown in section and with part of the top cut away to give a clear view of the pinion block. The full top part of the base is shown schematically in FIG. 3. The base is relatively massive and preferably is made of metal, for example, aluminum. The top part of the base serves as a pinion case and a pinion block 2 is pivotally mounted thereon, the mounting being through a dowel or pin 3 projecting into the side wall (not shown) of the pinion case. The upper surface of the pinion block is designed so that it will provide appropriate securing means, when used in cooperation with the handle as hereinafter described, for the particular members to be assembled by the apparatus. Thus, in the particular embodiment illustrated, a post-shaped key 4 is integrally attached to the upper surface of the pinion block and this key is so positioned that the profile of the said upper surface defines two grooves 5, 7, whose function will be described hereinafter.

The pinion block is biased in the position shown in FIG. 1 (the rest position) by the force of a compression spring 8 mounted in a hollow tubular member 9 having a proximal end 10 which is integral with the solid base 1. A representative spring for use in the invention is a helical spring made from 0.125 inch square wire having a maximum free length of about 2.725 inch, an outside diameter of about 0.485 inch, an inside diameter of about 0.220 inch and an estimated rating of about 1760 lb/inch nominal. Such a spring is capable of provide a biasing or torquing force of about 220 inch lb. The biasing force bears against the surface of the pinion block through biasing means comprising a cylindrically shaped tappet 11 whose distal end is attached to the proximal end of the compression spring, a first roller 12 attached to the proximal end of said tappet, which first roller bears against a second roller 13 attached to the surface of the pinion block. The compression spring is chosen so that the torque required to overcome the biasing force matches the torque desired for assembling the chosen threaded members.

Illustrated in FIG. 2 is a spring clip 14, held to the pinion case by a pair of screws 15, which bears against the edge of the pinion block to provide an audible click when the pinion block is pivoted to the fully torqued position.

A the securing means to hold the engageable members is provided by a handle 16 which is pivotally mounted at its distal end 17 on a foot 18 attached to the distal end of the hollow tubular member. The foot 18 is attached to the tubular member by a set screw 36. A leaf spring 19 is attached by a screw 20 adjacent the proximal end of the handle. Said leaf spring has a slot 21 (see FIG. 5) positioned so that when the handle is in the closed position the key 4 on the pinion block passes through said slot. A slot 22 is also defined in the top of the handle to accommodate the end of the key when the handle is closed.

A spring clip 23 is attached to the handle through screw 24. When the handle is in the closed position (see FIG. 9) the spring clip 23 clips around the tubular member 9 and thus maintains the assembly in the closed position.

Figure 9:
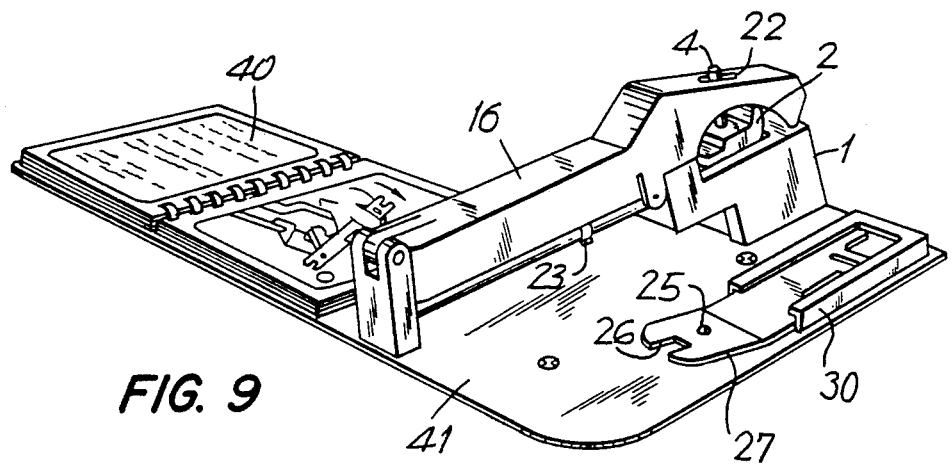
FIG. 9 is a panoramic presentation of a table-top version of the apparatus of the invention.

The preferred embodiment of the torque limiter assembly of the invention illustrated in FIGS. 1 to 6 may be hand held. Another version of this embodiment may be mounted on a table top as illustrated in FIG. 9. A further version may be bolted to a control unit of an acoustic surgical system.

Figure 7:
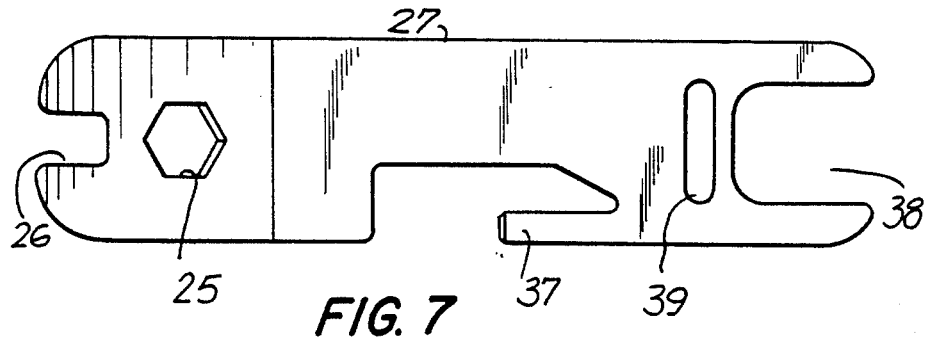
FIG. 7 is a plan view of a flat wrench suitable for use in the invention.
Figure 8:
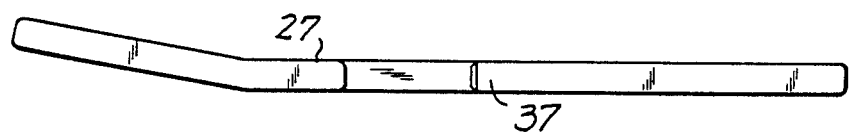
FIG. 8 is a side elevation of the wrench of FIG. 7.

A suitable wrench to be used in the apparatus of the invention is illustrated in FIGS. 7 and 8. The actual shape and size of each socket in the wrench will depend of course upon the configuration of the threaded member upon which it is to be used and it is to be understood that the sockets illustrated are given by way of example only. For said purpose of example, the hexagonal socket 25 and the rectangular socket 26 have been chosen to accommodate the hexagonal nut 25' and flat 26', respectively, of the threaded members illustrated in FIG. 10. The wrench illustrated in FIG. 7 also includes a keying pin 37 for aligning the connecting member 30 with a nose cone (not shown); a socket 38 for assembling an angled handpiece member (not shown); and a retaining notch 39 which cooperates with the curved part of spring clip 29 to hold the wrench in slot 28 (FIG. 1).

A flat wrench such as that illustrated in FIGS. 7 and 8 is convenient because it may be easily stored, either in a suitable slot 28 in the base of the assembly, where it is retained by the snapping engagement of spring clip 29 in notch 39, or in a suitable holster 30 as illustrated in the table top embodiment of FIG. 9.

As illustrated in FIG. 9, the table top embodiment includes the torque limiter assembly comprising the pinion block 2 mounted on base 1, a holster 30 for holding a wrench 27 and an instruction manual 40; all mounted on a convenient table top surface 41.

Figure 10:
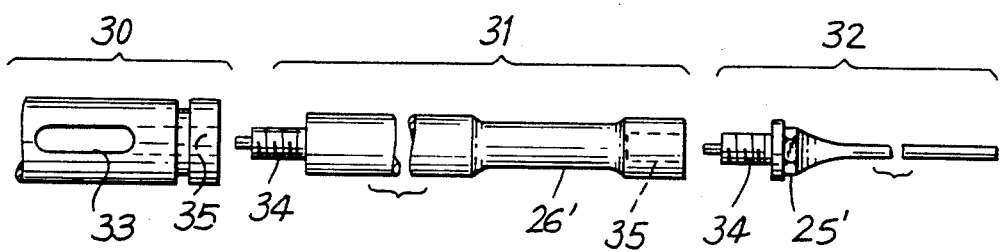
FIG. 10 illustrates, in exploded form, three threadably engageable members of an acoustic surgical device which does not form part of the invention but is included to show the manner in which the invention may be performed.

An acoustic device such as that of which a part is illustrated in FIG. 10 is typical of the type of device which may be assembled, and disassembled, by the apparatus of the present invention. The three members illustrated comprise a connecting member 30, an extension member 31 and an elongated tool member 32. The extension member is optional but is included for completeness of illustration.

The connecting member has a slot 33 which is elongated longitudinally parallel to its axis and extends radially through the member. A male threaded portion 34 at the proximal end of the extension member threads into a cooperating female thread, shown by dotted lines 35, in the distal end of the connecting member to connect the extension member to the connecting member; and a similar male thread 34 threaded into a female thread 35 connects the tool member to the extension or directly to the connecting member if the extension is not used.

In order to assemble the aforesaid members with the correct torque using the apparatus of the invention the first member is held in the securing means. Thus, to secure the connecting member 30, the handle 16 is held in the open position, the slot 33 is slid over the key 4 and the handle is placed in the closed position where the spring 19 presses down on the connecting member and holds it firmly in the securing means. The second member to be assembled is then screwed by hand on to the connecting member until it is finger tight. The wrench is then applied to the second member by the appropriate socket and is turned clockwise until the pinion block pivotally rocks from the rest position to the torqued position, as shown by the dotted lines T in FIG. 2. The torqued position is indicated audibly by a noticeable click and visually by movement of the key 4. The construction of the torque limiter assembly is such that is not possible to overtorque the joint with normal usage, i.e. unless the apparatus is abused by the use of excessive force after the click is heard.

To connect the tool member to the extension member the latter is held in the securing means by placing the flat portion 26' in the groove 5, holding it in place by closing the handle as described above for the connecting member and following the same assembly steps. The groove 7 is provided to accommodate and secure a member having a different size flat. It is to be understood that the dimensions and arrangement of key and grooves may be chosen to provide securing means to hold members of any desired size and configuration.

The members assembled as described above will be fastened together at the correct torque and can not be unscrewed by hand.

To disassemble the members the device is simply held in the securing means as before, the wrench is applied and turned in a counterclockwise direction to unscrew the relevant threaded engagement.

We claim:

1. An apparatus for assembling and disassembling a device comprising at least a first and a second threadably engageable member, which apparatus comprises:
   (a) wrenching means and
   (b) an integral securing means and torque limiter assembly; said assembly comprising, in combination, securing means operatively associated with a pinion block pivotally mounted on a solid base, said pinion block having a surface which bears against biasing means connected to force means which provides a predetermined amount of torquing when said first member is held in said securing means and said second member is turned relative thereto by said wrenching means, whereby the amount of torquing is limited by the pivotal movement of said pinion block.

2. An apparatus according to claim 1, in which said force means comprises a compression spring.

3. An apparatus according to claim 2, in which said compression spring has a proximal end and a distal end and is mounted in a hollow tubular member having a proximal end and a distal end, and said biasing means comprises a cylindrically shaped tappet having a distal end attached to the proximal end of said compression spring and a proximal end having a first roller attached thereto which first roller bears against a second roller attached to said surface of said pinion block.

4. An apparatus according to claim 3, in which the securing means comprises, in combination, a handle having a proximal end and a distal end and being pivotally mounted at said distal end on an arm attached to the distal end of said hollow tubular member such that the pivotal movement of the handle defines an open position and a closed position, respectively, relative to the pinion block, a leaf spring having a central slot and being attached near the proximal end of the handle on the side facing the pinion block, and a post-shaped key integrally attached to the upper surface of the pinion block at a position such that said key passes through the slot in the leaf spring when the handle is in the closed position.

5. An apparatus according to claim 4, in which said handle has a spring clip which clips around said tubular member when the handle is in the closed position, thereby maintaining the assembly in the closed position until said spring clip is released.

6. An apparatus according to claim 4, in which said key is so positioned on the upper surface of the pinion block that the profile of said upper surface defines grooves which, together with said key, are adapted to hold engageable members of different sizes.

7. An apparatus according to claim 1 which includes a spring clip which bears against an edge of the pinion block to provide an audible click when the pinion block is pivoted to the fully torqued position.

8. An apparatus according to claim 1, in which the integral securing means and torque limiter assembly is adapted to be hand held.

9. An apparatus according to claim 1, in which the integral securing means and torque limiter assembly is adapted to be mounted on a table top or bolted to a control unit of an acoustic surgical system.

10. An apparatus according to claim 1, in which said wrenching means comprises a simple flat wrench.

11. An apparatus according to claim 10, in which said wrench includes sockets of different sizes adapted to accommodate the appropriate flats of various members of an acoustic surgical device and also includes a notch to enable the wrench to be retained for storage by a cooperating spring clip located in the base of the integral securing means and torque limiter assembly.

* * * * *